United States Patent
Wu et al.

(10) Patent No.: US 10,508,279 B2
(45) Date of Patent: Dec. 17, 2019

(54) **RECOMBINANT *ESCHERICHIA COLI* FOR HIGH EFFICIENCY PRODUCTION OF FRUCTOSYLATED CHONDROITIN AND METHOD FOR MAKING THEREOF**

(71) Applicants: Jing Wu, Wuxi (CN); Quan Zhang, Wuxi (CN); Liming Liu, Wuxi (CN); Xiulai Chen, Wuxi (CN); Jia Liu, Wuxi (CN); Qiuling Luo, Wuxi (CN)

(72) Inventors: Jing Wu, Wuxi (CN); Quan Zhang, Wuxi (CN); Liming Liu, Wuxi (CN); Xiulai Chen, Wuxi (CN); Jia Liu, Wuxi (CN); Qiuling Luo, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 37 days.

(21) Appl. No.: 15/891,564

(22) Filed: Feb. 8, 2018

(65) Prior Publication Data
US 2019/0032062 A1   Jan. 31, 2019

(30) Foreign Application Priority Data
Jul. 26, 2017   (CN) .......................... 2017 1 0616371

(51) Int. Cl.
| C12N 1/20 | (2006.01) |
| C12N 15/70 | (2006.01) |
| C12N 9/10 | (2006.01) |
| C12N 9/90 | (2006.01) |
| C12P 19/24 | (2006.01) |
| C12P 19/26 | (2006.01) |

(52) U.S. Cl.
CPC .......... *C12N 15/70* (2013.01); *C12N 9/1096* (2013.01); *C12N 9/90* (2013.01); *C12P 19/24* (2013.01); *C12P 19/26* (2013.01); *C12Y 504/0201* (2013.01)

(58) Field of Classification Search
CPC .................................................... C12N 9/1096
See application file for complete search history.

(56) References Cited

U.S. PATENT DOCUMENTS 9,758,803 B2 *   9/2017   Merighi ................... C07H 1/00

* cited by examiner

*Primary Examiner* — Tekchand Saidha
(74) *Attorney, Agent, or Firm* — Lili Chen

(57) ABSTRACT

The present invention relates to the field of biotechnology engineering. It provides a recombinant *Escherichia coli* that can produce fructosylated chondroitin with high yields and the method for constructing the recombinant strain. The present invention discloses a method for constructing an expression plasmid pETM6R1-RBS-glmM-GGGS-glmS that contains a glmM and a glmS gene under regulation of ribosome binding sites. The recombinant plasmid was transformed into *E. coli* K4 to obtain a recombinant *E. coli* strain ZQ33 that can produce fructosylated chondroitin up to 3.99 g·L$^{-1}$ by fed-batch fermentation in a 5-L fermentor, which was increased by 108.90% compared to that of the wild type strain.

10 Claims, 4 Drawing Sheets

Specification includes a Sequence Listing.

RECOMBINANT *ESCHERICHIA COLI* FOR HIGH EFFICIENCY PRODUCTION OF FRUCTOSYLATED CHONDROITIN AND METHOD FOR MAKING THEREOF

CROSS-REFERENCES AND RELATED APPLICATIONS

This application claims the benefit of priority to Chinese Application No. 201710616371.6, entitled "A recombinant *Escherichia coli* for high efficiency production of fructosylated chondroitin and method for making thereof", filed Jul. 26, 2017 and which are herein incorporated by reference in the entirety.

BACKGROUND OF THE INVENTION

Field of the Invention

The invention relates to the field of biotechnology engineering, and more particularly relates to a recombinant *Escherichia coli* for efficient production of fructosylated chondroitin and the method for constructing the recombinant strain.

Description of the Related Art

Chondroitin sulfate (CS) is an unbranched acidic polysaccharide made of alternating units of D-glucuronic acid (D-GlcUA) and N-acetyl-galactosamine (GalNAc) connected by β-1,3 bond and β-1,4 bond. It is widely distributed in human cartilage, tendon, disc and other connective tissues. CS, hyaluronic acid, heparin, and keratan sulfate can make glycosaminoglycans. CS and its analogues have a variety of biological activity and medicinal value. They are clinically used to treat rheumatism and arthritis and confer cartilage anti-deformability and gel-like properties. They are so called human body's "soft gold". In addition, CS and analogues can be used as dietary supplement and humectants in the fields of food and cosmetics.

At present, the main method for industrial production of chondroitin sulfate and analogues is extraction from animal tissues, such as animal cartilage of pigs, cattle, sharks, etc., by alkali hydrolysis and protease hydrolysis. However, the extraction method has many problems, such as the restricted supply of raw materials, complicated production technology, unstable product quality, low level of industrialization and serious environmental pollution, which severely limit the development of industrial production of chondroitin sulfate and analogues. Therefore, domestic and foreign scholars continue to search for microbial fermentation methods for efficient production of chondroitin sulfate and analogues.

In recent years, researchers have systematically studied the production of chondroitin sulfate and its analogues using biochemical and metabolic engineering approaches. In 1988, it was found that the capsular polysaccharide from *Escherichia. coli* O10:K4:H4 is a chondroitin sulfate analogue (fructosylated chondroitin). In 1996, the yield of fructosylated chondroitin reached 300 $mg \cdot L^{-1}$ using the fermentation method. The yield of fructosylated chondroitin was further improved by overexpression of key enzymes such as chondroitin Polymerase KfoC and antiterminator RfaH. Further improving the yield of fructosylated chondroitin for industrial production is an urgent problem to be solved.

DESCRIPTION OF THE INVENTION

To solve the above problems, the present invention provides a recombinant *E. coli* that can produce high yield of fructosylated chondroitin and methods for producing fructosylated chondroitin using the recombinant strain. The present invention can efficiently produce fructosylated chondroitin via overexpressing key enzymes of fructosylated chondroitin synthesis pathway, laying a foundation for the industrial production of fructosylated chondroitin.

The present invention provides a recombinant *E. coli* that can produce fructosylated chondroitin efficiently, and the recombinant *E. coli* overexpresses phosphoglucosamine mutase and aminotransferase.

In one embodiment of the present invention, the phosphoglucosamine mutase and aminotransferase are connected to an expression vector through ribosome binding site 1 (RBS1), and the nucleotide sequence of the RBS1 is set forth in SEQ ID NO:5.

In one embodiment of the present invention, the phosphoglucosamine mutase is fused with the aminotransferase.

In one embodiment of the present invention, the amino acid sequence of said phosphoglucosamine mutase is set forth in SEQ ID NO:1, and the amino acid sequence of said aminotransferase is set forth in SEQ ID NO:2.

In one embodiment of the present invention, the RBS1, the phosphoglucosamine mutase gene (glmM), the linker GGGS and the aminotransferase gene (glmS) are fused together sequentially, and the fused gene is inserted into an expression vector whose nucleotide sequence is set forth in SEQ ID NO:7. The nucleotide sequence of RBS1 is set forth in SEQ ID NO:5, and the nucleotide sequence of the linker GGGS is set forth in SEQ ID NO:6.

In one embodiment of the present invention, the host of the recombinant *E. coli* is *E. coli* K4 ATCC23502.

The present invention provides a method of constructing a recombinant *E. coli* producing fructosylated chondroitin, comprises the following steps:

(1) obtaining the gene of phosphoglucosamine mutase whose amino acid sequence is set forth in SEQ ID NO:1, and the gene of aminotransferase whose amino acid sequence is set forth in SEQ ID NO:2;

(2) obtaining the DNA sequence of RBS1 whose nucleotide sequence is set forth in SEQ ID NO:5, and the DNA sequence of the linker GGGS whose nucleotide sequence is set forth in SEQ ID NO:6;

(3) obtaining the expression vector pETM6R1 whose nucleotide sequence is set forth in SEQ ID NO:7;

(4) fusing the RBS1, the phosphoglucosamine mutase gene, the linker GGGS and the aminotransferase gene together sequentially, and inserting the fused gene into expression vector pETM6R1 to obtain a recombinant plasmid pETM6R1-RBS1-glmM-GGGS-glmS;

(5) introducing the recombinant plasmid in step (4) into *E. coli* K4 ATCC 23502 to obtain a recombinant *E. coli*.

The present invention also provides a method of producing fructosylated chondroitin by batch fermentation of said recombinant *E. coli*. The fermentation medium contains 10 $g \cdot L^{-1}$ glycerol, 1 $g \cdot L^{-1}$ soy peptone, 2 $g \cdot L^{-1}$ $KH_2PO_4$, 10 $g \cdot L^{-1}$ $K_2HPO_4$, 0.1 $g \cdot L^{-1}$ $MgCl_2$, 1 $g \cdot L^{-1}$ $(NH_4)_2SO_4$, and 0.5 $g \cdot L^{-1}$ sodium citrate; the feeding medium contains 400 $g \cdot L^{-1}$ glycerol, 40 $g \cdot L^{-1}$ soy peptone; and the method is performed by cultivating the recombinant strain with a fed-batch fermentation at 37° C.

In one embodiment of the present invention, said batch fermentation is performed in a 5-L bioreactor with an inoculation ratio of 5-15%; 0.05-0.15 mmol IPTG is added to induce the expression of exogenous genes at 5-10 hr after inoculation, and the inducing temperature is 35-38° C.

In one embodiment of the present invention, the feeding strategy used in the fermentation is pH-stat. The feeding starts when the dissolved oxygen suddenly rises during the fermentation process. When the pH exceeds 7.0, the feeding process starts. When pH falls below 7.0, the feeding process stops.

The present invention using the method of fusion gene expression to achieve high efficiency expression of phosphoglucosamine mutase and aminotransferase genes. The recombinant *E. coli* strain can improve the yield of fructosylated chondroitin. Compared to the wild type *E. coli* K4 ATCC 23502, the yield of fructosylated chondroitin from recombinant strain is increased by 108.9% from 1.91 g·L$^{-1}$ to 3.99 g·L$^{-1}$. The method of the invention has great potential for increasing the yield of fructosylated chondroitin in industrial production.

EXAMPLES

Figure 1:
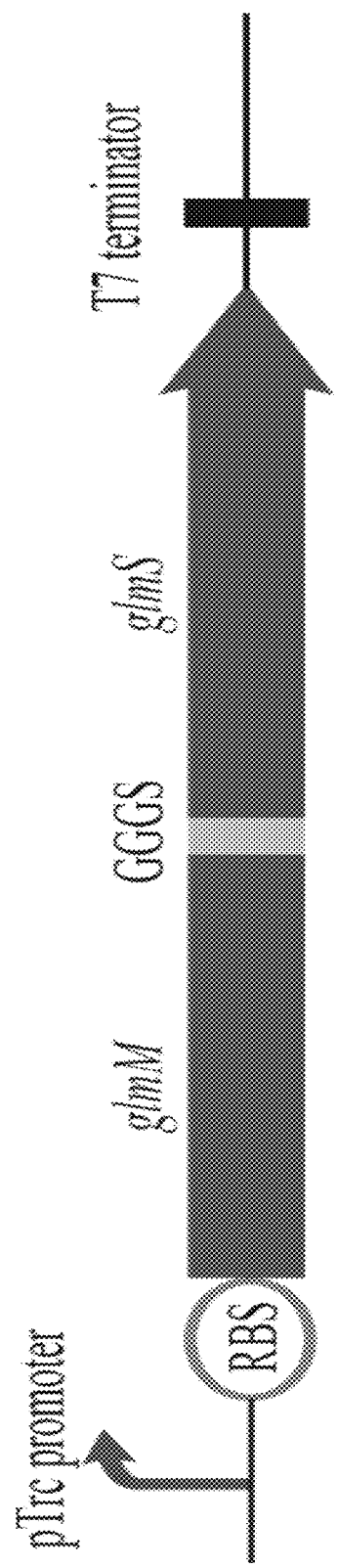
FIG. 1. Construction schematic of fused fragment of phosphoglucosamine mutase and aminotransferase.
Figure 2:
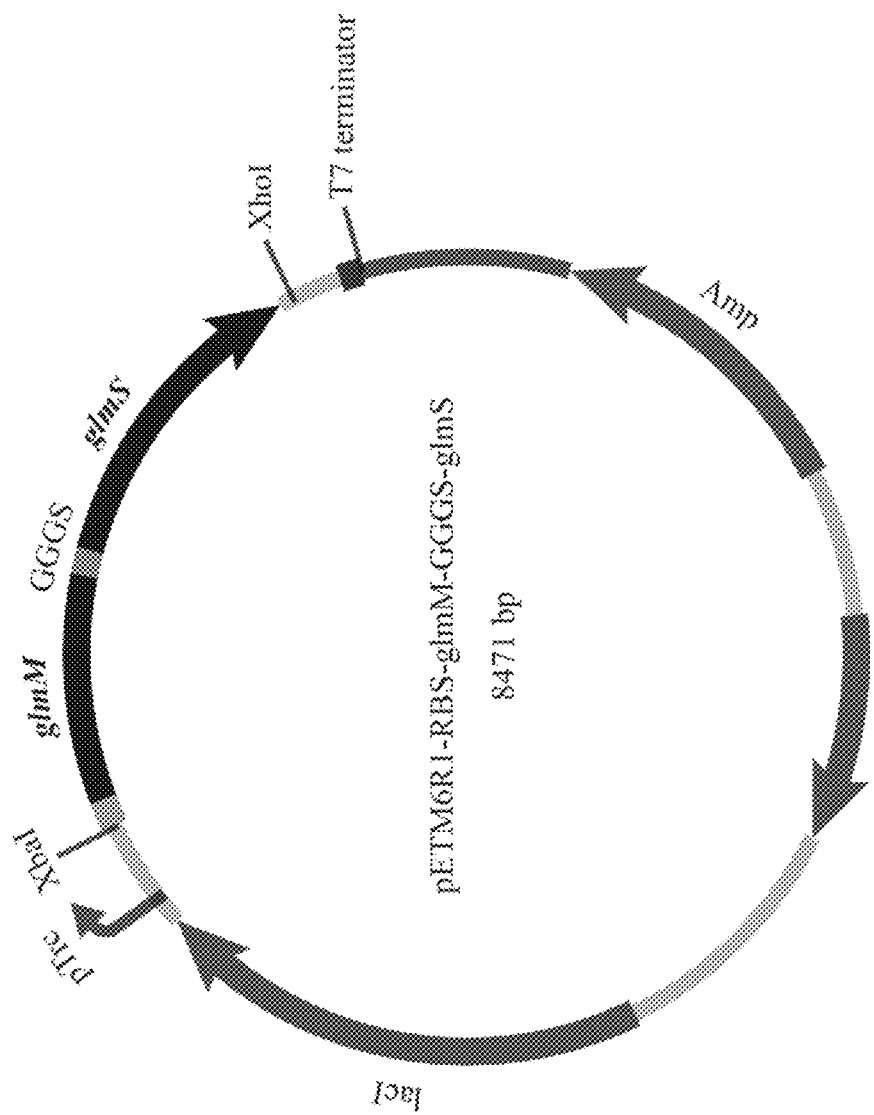
FIG. 2. The expression plasmid that contains phosphoglucosamine mutase and aminotransferase genes.

The following examples are intended for illustration purpose only, and not intended to limit the scope of the invention.
Materials and Methods:
Information of related nucleotide sequences:
(1) SEQ ID NO:1 is the amino acid sequence of phosphoglucosamine mutase from *Escherichia coli*.
(2) SEQ ID NO:2 is the amino acid sequence of aminotransferase from *Escherichia coli*.
(3) SEQ ID NO:3 is the nucleotide sequence of a regulatory DNA fragment RBS1-glmM-GGGS-glmS.
(4) SEQ ID NO:4 is the nucleotide sequence of inducible promoter pTrc.
(5) SEQ ID NO:5 is the nucleotide sequence of RBS1.
(6) SEQ ID NO:6 is the nucleotide sequence of GGGS.
(7) SEQ ID NO:7 is the nucleotide sequence of vector of pETM6R1.

The glucuronic acid of the fructosylated chondroitin was determined by the modified carbazole assay. The concentration of fructosylated chondroitin was 2.88 times of that of the glucuronic acid.

Example 1: Construction of the Fusion Fragment RBS1-glmM-GGGS-glmS

The phosphoglucosamine mutase glmM gene and the aminotransferase glmS gene were cloned from *Escherichia coli* K4 (ATCC23502). The *E. coli* K4 was inoculated into 25 mL Luria-Bertani (LB) liquid medium and cultured at 37° C., 200 rpm, for 12 hr. The bacterial cells were then harvested and the genomic DNA of the *E. coli* cells was extracted using a bacterial genomic DNA extraction kit.

Based on published genomic sequence database, primer pairs RH-glmM-S1/RH-glmM-A (SEQ ID NO:8/SEQ ID NO:9) and RH-glmS-S/RH-glmS-A (SEQ ID NO:10/SEQ ID NO:11) were designed for amplification of the glmM and the glmS gene, respectively. Using the extracted genomic DNA as template, the *E. coli*. glmM and the glmS gene were amplified by standard PCR.

The fusion fragment RBS1-glmM-GGGS-glmS was obtained via the standard fusion PCR amplification system using the glmM-S1/RH-glmS-A primer pair and the obtained glmM and glmS gene sequence as templates.

The nucleotide sequences of primers RH-glmM-S1 and RH-glmM-A, RH-glmS-S and RH-glmS-A were shown as follows (from 5' to 3'):

```
RH-glmM-S1:
GCTCTAGAAAGAGGGCGCGGCAGAGAAGGAGGAGGTAAGAAAT

GAGTAATCGTAAATATTTCGGT

RH-glmM-A:
CGCCAACAATTCCACACATAGAACCACCACCAACGGCTTTTACTG

CATCG

RH-glmS-S:
CGATGCAGTAAAAGCCGTTGGTGGTGGTTCTATGTGTGGAATTGTT

GGCG

RH-glmS-A:
CCGCTCGAGTTACTCAACCGTAACCGATTTTG
```

The fusion fragment RBS1-glmM-GGGS-glmS was purified using agarose gel electrophoresis and the purified product was ligated into the pMD19 T vector. The ligation system (total 10 μL) contained: 5 μL ligase solution, 4 μL the fusion fragment, 1 μL The pMD19 T vector. The ligation reaction was performed at 16° C. overnight. The ligated product was transformed into JM109 competent cells. Single colonies were picked up and positive transformants were confirmed by PCR amplification and DNA sequencing analysis. The successfully constructed recombinant plasmid was named as pMD19-RBS1-glmM-GGGS-glmS.

Example 2: Construction of the Fusion Fragment RBS2-glmM-GGGS-glmS

Fusion fragment RBS2-glmM-GGGS-glmS and RBS3-glmM-GGGS-glmS were obtained by the same method of Example 1, with the primer RH-glmM-S 1 substituted by RH-glmM-S2 (SEQ ID NO:12) and RH-glmM-S3 (SEQ ID NO:13), respectively.

The nucleotide sequences of primers RH-glmM-S2 and RH-glmM-S3 were shown as follows (from 5' to 3'):

```
RH-glmM-S2 (SEQ ID NO: 12):
GCTAGATATTTAAACTATCACGACATAAGGAGGTC

AGGGATGAGTAATCGTAAATATTTCGGT

RH-glmM-S3 (SEQ ID NO: 13):
GCTCTAGACGACATAACGTTAGAAAAGAATAAGG

TAGTTTCATGAGTAATCGTAAATATTTCGGT
```

Example 3: Construction of the Expression Plasmid pETM6R1

Promoter pTrc was cloned from vector pTrcHisA by standard PCR amplification using primer pair pTrcHisA-S/pTrcHisA-A (SEQ ID NO:14/SEQ ID NO:15).

The nucleotide sequences of primer pair pTrcHisA-S and pTrcHisA-A were shown as follows (from 5' to 3'):

```
pTrcHisA-S (SEQ ID NO: 14):
CCCTAGGATCGAGATCGATCTCGATCCCGCGAAATT

AATACGACTCACTATATTGACAATTAATCATCCGG pTrcHisA-A (SEQ ID NO: 15):
GCTCTAGAGGTAATTTTTAATAATAAAGTTAATCG
```

The pTrc gene fragment and pETM6 vector were digested by restriction enzymes AvrII and XbaI, respectively. The digested fragments were purified by agarose gel electrophoresis and the purified fragments were used for ligation. The ligation products was transformed into JM109 competent cells and positive recombinant plasmid was verified by sequencing. The recombinant vector was designated as pETM6R1.

Example 4: Construction of the Recombinant Plasmid pETM6R1-RBS1-glmM-GGGS-glmS The *E. coli* JM109 strain that carried recombinant plasmid pMD19-RBS1-glmM-GGGS-glmS was incubated in 25 mL LB media at 37° C., 200 rpm for 12 hours, and the plasmid DNA was extracted by a plasmid DNA extraction kit. In Example 1, XbaI and XhoI restriction site were introduced into the RH-glmM-S1 and the RH-glmS-A primer, respectively. The recombinant plasmid pMD19-RBS1-glmM-GGGS-glmS and pETM6R1 were digested with XbaI and XhoI. The digested fragments were purified and ligated together. Then, the obtained ligation product was transformed into JM109 competent cells. The positive recombinant cells were verified by sequencing, and the recombinant plasmid was designated as pETM6R1-RBS1-glmM-GGGS-glmS. Finally, extracted recombinant plasmid was transformed into *E. coli* K4, and the positive recombinant *E. coli* K4 carrying pETM6R1-RBS1-glmM-GGGS-glmS was designated as ZQ33.

Example 5: Construction of the Recombinant Plasmid pETM6R1-RBS2-glmM-GGGS-glmS, pETM6R1-RBS3-glmM-GGGS-glmS Using the same method as described in Example 4, fusion fragment RBS2-glmM-GGGS-glmS and RBS3-glmM-GGGS-glmS were insert into pETM6R1 to obtain plasmid pETM6R1-RBS2-glmM-GGGS-glmS and pETM6R1-RBS3-glmM-GGGS-glmS, respectively. The recombinant plasmids were transformed into *E. coli* K4 and the recombinant strains carrying plasmid pETM6R1-RBS2-glmM-GGGS-glmS and pETM6R1-RBS3-glmM-GGGS-glmS were designated as ZQ31 and ZQ32, respectively.

Example 6: Fermentation of the Recombinant Strains in a Shake Flask

Recombinant strains ZQ31, ZQ32 and ZQ33 were fermented, respectively. Single colonies of the recombinant strains were grown in a LB media with 10 mg·mL$^{-1}$ ampicillin at 37° C., 200 rpm for 10 hr. The seed cultures were transferred to a shake flask with a 1% inoculation volume. The cultivation in shake flask was performed on a rotary shaker at 200 rpm at 37° C. The inducer isopropyl β-D-1-thiogalactopyranoside (IPTG, 0.04 mmol) was added to induce the expression of exogenous glmM and glmS gene after 5 hr incubation at 37° C. Fermentation samples were periodically withdrawn to determine the fructosylated chondroitin production. The sample was centrifuged at 10,000 rpm for 15 min, the fermentation supernatant was transferred to another tube, and 3 volumes ethanol was added to precipitate fructosylated chondroitin at 4° C. for 10 hr. The precipitate was collected by centrifugation (10,000 rpm for 10 min) and dissolved in ultra-pure water. The suspension was used for determination of the yield of fructosylated chondroitin.

Figure 3:
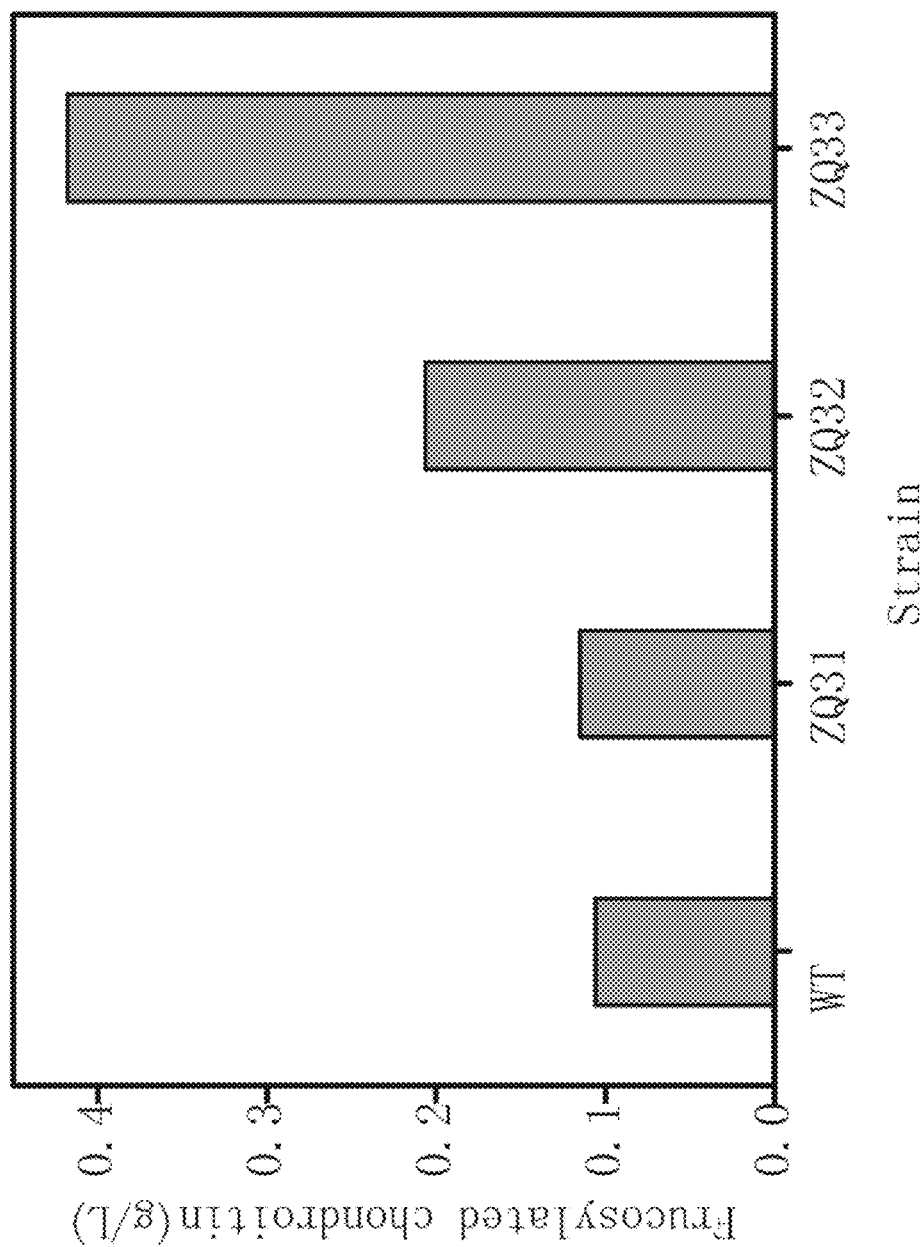
FIG. 3. The production of fructosylated chondroitin using the recombinant strain and the wild type *E. coli* K4 strain cultured in a shake flask.

FIG. 3 showed the yield of fructosylated chondroitin in fermentation with the recombinant strains ZQ31, ZQ32, ZQ33 and *E. coli* K4 were 0.115, 0.206, 0.418 and 0.106 g·L$^{-1}$, respectively. The fructosylated chondroitin yields in all the recombinant strains were higher than that of *E. coli* K4.

Figure 4:
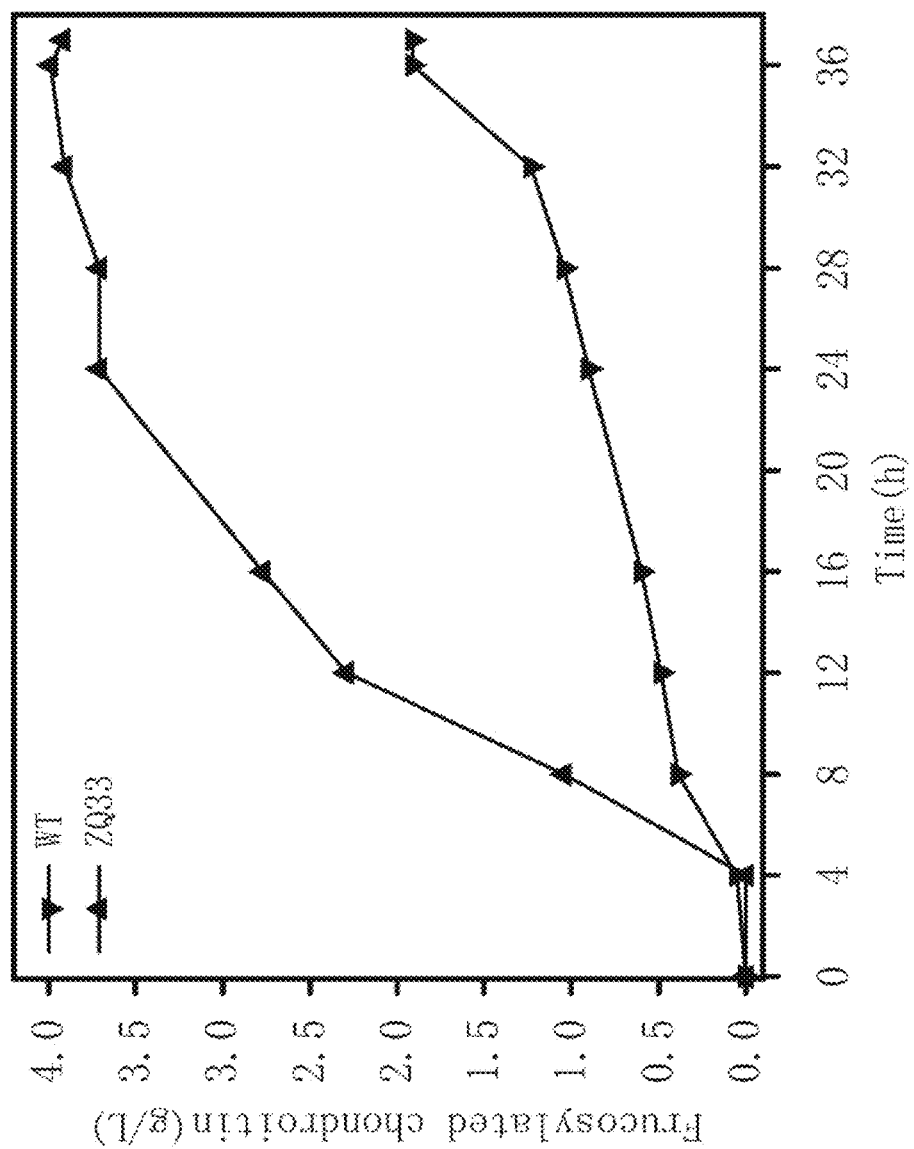
FIG. 4. The production of fructosylated chondroitin using the recombinant strain ZQ33 and the wild type *E. coli* K4 strain cultured in a 5-L fermentor.

Example 7: Fed-Batch Fermentation of the Recombinant Strain ZQ33 in a 5-L Fermentor Recombinant strain ZQ33 was selected for Fed-batch fermentation, which was performed in a 5-L bioreactor by a pH-stat control mode. The initial volume was 2.5 L and the inoculation ratio was 10%. The temperature was maintained at 37° C. and the pH was controlled at 7.0 by aqueous ammonia. The medium for cultivation contained 10 g·L$^{-1}$ glycerol, 1 g·L$^{-1}$ soy peptone, 2 g·L$^{-1}$ KH$_2$PO$_4$, 10 g·L$^{-1}$ K$_2$HPO$_4$, 0.1 g·L$^{-1}$ MgCl$_2$, 1 g·L$^{-1}$ (NH$_4$)$_2$SO$_4$, and 0.5 g·L$^{-1}$ sodium citrate. The feeding medium contained 400 g·L-1 glycerol, and 40 g·L-1 soy peptone. The fed-batch fermentation strategy uses fermentation pH as a feeding indicator. When glycerol was consumed during the fermentation and dissolved oxygen level showed a sharp increase, which leads to the pH increase to over 7 and triggers the start of feeding. When the culture pH drops to below 7, the feeding process stops. This feeding strategy continues until the end of the fermentation. IPTG was added to induce the expression of exogenous genes after 5 hr of fermentation. The yield of fructosylated chondroitin was measured every 4 hr as described in Example 6. FIG. 4 showed the yield of fructosylated chondroitin of the recombination strain ZQ33 and *E. coli* K4. The recombinant strain ZQ33 and *E. coli* K4 could generate fructosylated chondroitin up to 3.99 g·L$^{-1}$ and 1.91 g·L$^{-1}$ at 36 hr of fermentation, respectively.

While the present invention has been described in some detail for purposes of clarity and understanding, one skilled in the art will appreciate that various changes in form and detail can be made without departing from the true scope of the invention, which is defined by the appended claims. All figures, tables, appendices, patents, patent applications and publications, referred to above, are hereby incorporated by reference.

What is claimed is:

1. A recombinant *E. coli* that can produce fructosylated chondroitin with high efficiency, wherein said recombinant *E. coli* overexpresses phosphoglucosamine mutase and aminotransferase.

2. The recombinant *E. coli* of claim 1, wherein the amino acid sequence of said phosphoglucosamine mutase is set forth in SEQ ID NO:1, and the amino acid sequence of said aminotransferase is set forth in SEQ ID NO:2.

3. The recombinant *E. coli* of claim 1, wherein said recombinant *E. coli* contains an phosphoglucosamine mutase gene (glmM) and an aminotransferase gene (glmS) connected to an expression vector through RBS1, wherein the nucleotide sequence of said RBS1 is set forth in SEQ ID NO: 5.

4. The recombinant *E. coli* of claim 3, wherein said glmM is fused and co-expressed with said glmS.

5. The recombinant *E. coli* of claim 3, wherein said RBS1, said glmM, a linker GGGS and said glmS are fused together sequentially, which is inserted into said expression vector whose nucleotide sequence is set forth in SEQ ID NO:7, and wherein the nucleotide sequence of said GGGS linker is set forth in SEQ ID NO:6.

6. The recombinant *E. coli* of claim 1, wherein the host strain of said recombinant *E. coli*. is *E. coli* K4 ATCC23502.

7. A method for constructing a recombinant *E. coli* of claim 1, comprises the following steps:
  1) obtaining the gene of phosphoglucosamine mutase whose amino acid sequence is set forth in SEQ ID NO:1, and the gene of aminotransferase whose amino acid sequence is set forth in SEQ ID NO:2;
  2) obtaining the gene of RBS1 whose nucleotide sequence is set forth in SEQ ID NO:5, and the DNA sequence of a linker GGGS whose nucleotide sequence is set forth in SEQ ID NO:6;
  3) obtaining the expression vector pETM6R1 whose nucleotide sequence is set forth in SEQ ID NO:7;
  4) fusing said RBS1, said phosphoglucosamine mutase gene, said linker GGGS and said aminotransferase gene together sequentially, and inserting the fused gene into said expression vector pETM6R1 to obtain a recombinant plasmid pETM6R1-RBS1-glmM-GGGS-glmS;
  5) introducing said recombinant plasmid pETM6R1-RBS1-glmM-GGGS-glmS into *E. coli* K4 ATCC23502 to obtain said recombinant *E. coli* that produces high yield fructosylated chondroitin.

8. A method of producing fructosylated chondroitin by batch fermentation, comprising cultivating the recombinant *E. coli* of claim 1 in said batch fermentation, wherein fermentation medium used in said batch fermentation contains 10 $g·L^{-1}$ glycerol, 1 $g·L^{-1}$ soy peptone, 2 $g·L^{-1}$ $KH_2PO_4$, 10 $g·L^{-1}$ $K_2HPO_4$, 0.1 $g·L^{-1}$ $MgCl_2$, 1 $g·L^{-1}$ $(NH_4)_2SO_4$, and 0.5 $g·L^{-1}$ sodium citrate; and feeding medium of said batch fermentation contains 400 $g·L^{-1}$ glycerol, 40 $g·L^{-1}$ soy peptone; and wherein said batch fermentation is performed at 37° C. using a fed-batch fermentation strategy.

9. The method of claim 8, wherein said batch fermentation is performed in a 5-L bioreactor with an inoculation ratio of 5-15%; inducer of 0.05-0.15 mmol IPTG is added to induce the expression of exogenous genes at 5-10 hr after inoculation; and the inducing temperature is 35-38° C.

10. The method of claim 8, wherein said batch fermentation is performed in a 5-L bioreactor with a feeding medium under a pH-stat control strategy, wherein feeding starts when there is a sudden increase of dissolved oxygen and pH exceeds 7.0 during the fermentation, and the feeding stops when the pH falls below 7.0.

* * * * *

SEQUENCE LISTING

<160> NUMBER OF SEQ ID NOS: 15

<210> SEQ ID NO 1

<211> LENGTH: 445
<212> TYPE: PRT
<213> ORGANISM: Escherichia coli K4 ATCC 23502

<400> SEQUENCE: 1

```
Met Ser Asn Arg Lys Tyr Phe Gly Thr Asp Gly Ile Arg Gly Arg Val
1               5                   10                  15

Gly Asp Ala Pro Ile Thr Pro Asp Phe Val Leu Lys Leu Gly Trp Ala
            20                  25                  30

Ala Gly Lys Val Leu Ala Arg His Gly Ser Arg Lys Ile Ile Ile Gly
        35                  40                  45

Lys Asp Thr Arg Ile Ser Gly Tyr Met Leu Glu Ser Ala Leu Glu Ala
    50                  55                  60

Gly Leu Ala Ala Ala Gly Leu Ser Ala Leu Phe Thr Gly Pro Met Pro
65                  70                  75                  80

Thr Pro Ala Val Ala Tyr Leu Thr Arg Thr Phe Arg Ala Glu Ala Gly
                85                  90                  95

Ile Val Ile Ser Ala Ser His Asn Pro Phe Tyr Asp Asn Gly Ile Lys
            100                 105                 110

Phe Phe Ser Ile Asp Gly Thr Lys Leu Pro Asp Ala Val Glu Glu Ala
        115                 120                 125

Ile Glu Ala Glu Met Glu Lys Glu Ile Ser Cys Val Asp Ser Ala Glu
    130                 135                 140

Leu Gly Lys Ala Ser Arg Ile Val Asp Ala Ala Gly Arg Tyr Ile Glu
145                 150                 155                 160

Phe Cys Lys Ala Thr Phe Pro Asn Glu Leu Ser Leu Ser Glu Leu Lys
                165                 170                 175

Ile Val Val Asp Cys Ala Asn Gly Ala Thr Tyr His Ile Ala Pro Asn
            180                 185                 190

Val Leu Arg Glu Leu Gly Ala Asn Val Ile Ala Ile Gly Cys Glu Pro
        195                 200                 205

Asn Gly Val Asn Ile Asn Ala Glu Val Gly Ala Thr Asp Val Arg Ala
    210                 215                 220

Leu Gln Ala Arg Val Leu Ala Glu Lys Ala Asp Leu Gly Ile Ala Phe
225                 230                 235                 240

Asp Gly Asp Gly Asp Arg Val Ile Met Val Asp His Glu Gly Asn Lys
                245                 250                 255

Val Asp Gly Asp Gln Ile Met Tyr Ile Ile Ala Arg Glu Gly Leu Arg
            260                 265                 270

Gln Gly Gln Leu Arg Gly Gly Ala Val Gly Thr Leu Met Ser Asn Met
        275                 280                 285

Gly Leu Glu Leu Ala Leu Lys Gln Leu Gly Ile Pro Phe Ala Arg Ala
    290                 295                 300

Lys Val Gly Asp Arg Tyr Val Leu Glu Lys Met Gln Glu Lys Gly Trp
305                 310                 315                 320

Arg Ile Gly Ala Glu Asn Ser Gly His Val Ile Leu Leu Asp Lys Thr
                325                 330                 335

Thr Thr Gly Asp Gly Ile Val Ala Gly Leu Gln Val Leu Ala Ala Met
            340                 345                 350

Ala Arg Asn His Met Ser Leu His Asp Leu Cys Ser Gly Met Lys Met
        355                 360                 365

Phe Pro Gln Ile Leu Val Asn Val Arg Tyr Thr Ala Gly Ser Gly Asp
    370                 375                 380

Pro Leu Glu His Glu Ser Val Lys Ala Val Thr Ala Glu Val Glu Ala
```

```
            385                 390                 395                 400
Ala Leu Gly Asn Arg Gly Arg Val Leu Leu Arg Lys Ser Gly Thr Glu
                    405                 410                 415

Pro Leu Ile Arg Val Met Val Glu Gly Glu Asp Glu Ala Gln Val Thr
                    420                 425                 430

Glu Phe Ala His Arg Ile Ala Asp Ala Val Lys Ala Val
                    435                 440                 445

<210> SEQ ID NO 2
<211> LENGTH: 608
<212> TYPE: PRT
<213> ORGANISM: Escherichia coli K4 ATCC 23502

<400> SEQUENCE: 2

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
                20                  25                  30

Gly Leu Ala Val Val Asp Ala Glu Gly His Met Thr Arg Leu Arg Arg
            35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
                100                 105                 110

Lys Ala Arg Gly Tyr Thr Phe Val Ser Glu Thr Asp Thr Glu Val Ile
                115                 120                 125

Ala His Leu Val Asn Trp Glu Leu Lys Gln Gly Gly Thr Leu Arg Glu
            130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
                180                 185                 190

Asp Gln Leu Ala Leu Leu Pro Val Thr Arg Arg Phe Ile Phe Leu Glu
                195                 200                 205

Glu Gly Asp Ile Ala Glu Ile Thr Arg Arg Ser Val Asn Ile Phe Asp
            210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
                260                 265                 270

Ser His Gly Gln Val Asp Leu Ser Glu Leu Gly Pro Asn Ala Asp Glu
            275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320
```

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
370                 375                 380

Glu Ser Asp Leu Ala Leu Met Thr Asn Ala Gly Thr Glu Ile Gly Val
385                 390                 395                 400

Ser Thr Lys Ala Phe Thr Thr Gln Leu Thr Val Leu Leu Met Leu Val
                405                 410                 415

Ala Lys Leu Ser Arg Leu Lys Gly Leu Asp Ala Ser Ile Glu His Asp
            420                 425                 430

Ile Val His Gly Leu Gln Ala Leu Pro Ser Arg Ile Glu Gln Met Leu
        435                 440                 445

Ser Gln Asp Lys Arg Ile Glu Ala Leu Ala Glu Asp Phe Ser Asp Lys
450                 455                 460

His His Ala Leu Phe Leu Gly Arg Gly Asp Gln Tyr Pro Ile Ala Leu
465                 470                 475                 480

Glu Gly Ala Leu Lys Leu Lys Glu Ile Ser Tyr Ile His Ala Glu Ala
                485                 490                 495

Tyr Ala Ala Gly Glu Leu Lys His Gly Pro Leu Ala Leu Ile Asp Ala
            500                 505                 510

Asp Met Pro Val Ile Val Ala Pro Asn Asn Glu Leu Leu Glu Lys
        515                 520                 525

Leu Lys Ser Asn Ile Glu Glu Val Arg Ala Arg Gly Gly Gln Leu Tyr
530                 535                 540

Val Phe Ala Asp Gln Asp Ala Gly Phe Val Ser Ser Asp Asn Met His
545                 550                 555                 560

Ile Ile Glu Met Pro His Val Glu Glu Val Ile Ala Pro Ile Phe Tyr
                565                 570                 575

Thr Val Pro Leu Gln Leu Leu Ala Tyr His Val Ala Leu Ile Lys Gly
            580                 585                 590

Thr Asp Val Asp Gln Pro Arg Asn Leu Ala Lys Ser Val Thr Val Glu
        595                 600                 605

<210> SEQ ID NO 3
<211> LENGTH: 3217
<212> TYPE: DNA
<213> ORGANISM: Artificial Sequence
<220> FEATURE:
<223> OTHER INFORMATION: Synthetic DNA

<400> SEQUENCE: 3
tctagaaaga gggcgcggca gagaaggagg aggtaagaaa tgagtaatcg taaatatttc      60
ggtaccgatg ggattcgtgg tcgtgtaggg gatgcgccga tcacacctga ttttgtgctt     120
aagctgggtt gggccgcggg taaagtgctg gcgcgccacg gctcccgtaa gatcattatt     180
ggtaaagaca cgcgtatttc tggctatatg ctggagtcag cactggaagc gggtctggcg     240
gcagcgggcc tttccgcact cttcactggc ccgatgccaa caccggccgt ggcttatctg     300
acgcgtacct ccgcgcaga ggccggaatt gtgatatctg catcgcataa cccgttctac     360
gataatggca ttaaattctt ctctatcgac ggcaccaaac tgccggatgc ggtagaagag     420
gccatcgaag cggaaatgga aaggagatc agctgcgttg attcggcaga actgggtaaa     480

-continued

```
gccagccgta tcgttgatgc cgcgggtcgc tatatcgagt tttgcaaagc cacgttcccg    540
aacgaactta gcctcagtga actgaagatt gtggtggatt gtgcaaacgg tgcgacttat    600
cacatcgcgc cgaacgtgct gcgcgaactg ggggcgaacg ttatcgctat cggttgtgag    660
ccaaacggtg taaacatcaa tgccgaagtg ggggctaccg acgttcgcgc gctccaggct    720
cgtgtgctgg ctgaaaaagc ggatctcggt attgccttcg acggcgatgg cgatcgcgtg    780
attatggttg accatgaagg caataaagtc gatggcgatc agatcatgta tatcatcgcg    840
cgtgaaggtc ttcgtcaggg ccagctgcgt ggtggcgctg tgggtacatt gatgagcaac    900
atggggcttg aactggcgct gaaacagtta ggaattccat ttgcgcgcgc gaaagtgggt    960
gaccgctacg tactggaaaa aatgcaggag aaaggctggc gtatcggtgc agagaattcc    1020
ggtcatgtga tcctgctgga taaaactact accggtgacg catcgttgc tggcttgcag    1080 gtgctggcgg ctatggcacg taaccatatg agcctgcacg accttttgcag cggcatgaaa    1140 atgttcccgc agattctggt taacgtacgt tacaccgcag gtagcggcga tccacttgag    1200
catgagtcag ttaaagccgt gaccgcagag gttgaagctg cgctgggcaa ccgtggacgc    1260
gtgttgctgc gtaaatccgg caccgaaccg ttaattcgcg tgatggtgga aggcgaagac    1320
gaagcgcagg tgactgaatt tgcacaccgc atcgccgatg cagtaaaagc cgttggtggt    1380
ggttctatgt gtggaattgt tggcgcgatc gcgcaacgtg atgtagcaga aatccttctt    1440
gaaggtttac gtcgtctgga ataccgcgga tatgactctg ccggtctggc cgttgttgat    1500
gcggaaggtc atatgacccg cctgcgtcgc ctcggtaaag tccagatgct ggctcaggca    1560
gcggaagaac atcctctgca tggcggcacc ggtattgctc atactcgctg ggcgacacac    1620 ggtgaaccttt cagaagtgaa tgcgcatccg catgtttctg aacacattgt ggtggtgcat    1680
aacggcatca tcgaaaacca tgaaccgctg cgtgaagagc taaaagcgcg tggctatacc    1740
ttcgtttctg aaaccgacac cgaagtgatt gcccatctgg tgaactggga gctgaaacaa    1800
ggcgggactc tgcgtgaggc cgttctgcgt gctatcccgc agctgcgtgg tgcgtacggt    1860
acagtgatca tggactcccg tcacccggat accctgctgg cggcacgttc tggtagtccg    1920
ctggtgattg gcctgggggat gggcgaaaac tttatcgctt ctgaccagct ggcgctgttg    1980
ccggtgaccc gtcgctttat cttccttgaa gagggcgata ttgcggaaat cactcgccgt    2040
tcggtaaaca tcttcgataa aactggcgcg gaagtaaaac gtcaggatat cgaatccaat    2100
ctgcaatatg acgcgggcga taaaggcatt taccgtcact acatgcagaa agagatctac    2160
gaacagccga acgcgatcaa aaacacccttt accggacgca tcagccacgg tcaggttgat    2220
ttaagcgagc tgggaccgaa cgccgacgaa ctgttgtcga aggttgagca tattcagatc    2280
ctcgcctgtg gtacttctta taactccggt atggtttccc gctactggtt tgaatcgcta    2340
gcaggtattc cgtgcgacgt cgaaatcgcc tctgaattcc gctatcgcaa atctgccgtg    2400
cgtcgtaaca gcctgatgat caccttgtca cagtctggcg aaaccgcgga taccctggct    2460
ggcctgcgtc tgtcgaaaga gctgggttac cttggttcac tggcaatctg taacgttccg    2520
ggttcttctc tggtgcgcga atccgatctg gcgctaatga ccaacgcggg tacagaaatc    2580
ggcgtggcat ccactaaagc attcaccact cagttaactg tgctgttgat gctggtggcg    2640
aagctgtctc gcctgaaagg tctggatgcc tccattgaac atgacattgt gcatggtctg    2700
caggcgttgc cgagccgtat tgagcagatg ctgtctcagg acaaacgcat tgaagctctg    2760
gcagaagatt tctctgacaa acatcacgcg ctgttcctgg gccgtggcga tcagtaccca    2820
```

| | |
|---|---|
| atcgcgctgg aaggcgcatt gaagctgaaa gagatctctt acattcacgc tgaagcctac | 2880 |
| gctgcaggtg aactgaaaca cggtccgctg gcgctgattg atgccgatat gccggttatc | 2940 |
| gtcgttgcac cgaacaacga attgctggaa aaactaaaat ccaacattga agaagttcgc | 3000 |
| gcgcgtggcg gtcagttgta tgtcttcgcc gatcaggatg cgggttttgt aagtagcgat | 3060 |
| aacatgcaca tcatcgagat gccgcatgtg aagaggtga ttgcaccaat cttctacacc | 3120 |
| gttccgctgc agctactggc ttatcacgtc gcgctgatca aggtaccga cgttgaccag | 3180 |
| ccgcgtaacc tggcaaaatc ggttacggtt gagtaac | 3217 |

<210> SEQ ID NO 4
<211> LENGTH: 234
<212> TYPE: DNA
<213> ORGANISM: Artificial Sequence
<220> FEATURE:
<223> OTHER INFORMATION: Synthetic DNA

<400> SEQUENCE: 4

| | |
|---|---|
| cctaggatcg agatcgatct cgatcccgcg aaattaatac gactcactat attgacaatt | 60 |
| aatcatccgg ctcgtataat gtgtggaatt gtgagcggat aacaatttca cacaggaaac | 120 |
| agcgccgctg agaaaaagcg aagcggcact gctctttaac aatttatcag acaatctgtg | 180 |
| tgggcactcg accggaatta tcgattaact ttattattaa aaattacctc taga | 234 |

<210> SEQ ID NO 5
<211> LENGTH: 33
<212> TYPE: DNA
<213> ORGANISM: Artificial Sequence
<220> FEATURE:
<223> OTHER INFORMATION: Synthetic DNA

<400> SEQUENCE: 5

| | |
|---|---|
| aagagggcgc ggcagagaag gaggaggtaa gaa | 33 |

<210> SEQ ID NO 6
<211> LENGTH: 12
<212> TYPE: DNA
<213> ORGANISM: Artificial Sequence
<220> FEATURE:
<223> OTHER INFORMATION: Synthetic DNA

<400> SEQUENCE: 6

| | |
|---|---|
| ggtggtggtt ct | 12 |

<210> SEQ ID NO 7
<211> LENGTH: 5351
<212> TYPE: DNA
<213> ORGANISM: Artificial Sequence
<220> FEATURE:
<223> OTHER INFORMATION: Synthetic DNA

<400> SEQUENCE: 7

| | |
|---|---|
| ttgacaatta atcatccggc tcgtataatg tgtggaattg tgagcggata acaatttcac | 60 |
| acaggaaaca gcgccgctga gaaaaagcga agcggcactg ctctttaaca atttatcaga | 120 |
| caatctgtgt gggcactcga ccggaattat cgattaactt tattattaaa aattacctct | 180 |
| agaaataatt ttgtttaact ttaagaagga gatatacata tggcagatct caattggata | 240 |
| tcggccggcc acgcgatcgc tgacgtcggt accctcgagt ctggtaaaga aaccgctgct | 300 |
| gcgaaatttg aacgccagca catgactcg tctactagtc gcagcttaat taacctaaac | 360 |
| tgctgccacc gctgagcaat aactagcata accccttggg gcctctaaac gggtcttgag | 420 |

-continued

```
gggttttttg ctagcgaaag gaggagtcga ctatatccgg attggcgaat gggacgcgcc    480
ctgtagcggc gcattaagcg cggcgggtgt ggtggttacg cgcagcgtga ccgctacact    540
tgccagcgcc ctagcgcccg ctcctttcgc tttcttccct tcctttctcg ccacgttcgc    600
cggctttccc cgtcaagctc taaatcgggg ctcccttta gggttccgat ttagtgcttt     660
acggcacctc gaccccaaaa aacttgatta gggtgatggt tcacgtagtg gccatcgcc     720 ctgatagacg gttttccgcc ctttgacgtt ggagtccacg ttctttaata gtggactctt    780
gttccaaact ggaacaacac tcaaccctat ctcggtctat tcttttgatt tataagggat    840
tttgccgatt tcggcctatt ggttaaaaaa tgagctgatt taacaaaaat ttaacgcgaa    900
ttttaacaaa atattaacgt ttacaatttc tggcggcacg atggcatgag attatcaaaa    960
aggatcttca cctagatcct tttaaattaa aaatgaagtt ttaaatcaat ctaaagtata   1020
tatgagtaaa cttggtctga cagttaccaa tgcttaatca gtgaggcacc tatctcagcg   1080
atctgtctat ttcgttcatc catagttgcc tgactcccg tcgtgtagat aactacgata    1140
cgggagggct taccatctgg ccccagtgct gcaatgatac cgcgagaccc acgctcaccg   1200
gctccagatt tatcagcaat aaaccagcca gccggaaggg ccgagcgcag aagtggtcct   1260
gcaactttat ccgcctccat ccagtctatt aattgttgcc gggaagctag agtaagtagt   1320
tcgccagtta atagtttgcg caacgttgtt gccattgcta caggcatcgt ggtgtcacgc   1380
tcgtcgtttg gtatggcttc attcagctcc ggttcccaac gatcaaggcg agttacatga   1440
tcccccatgt tgtgcaaaaa agcggttagc tccttcggtc ctccgatcgt tgtcagaagt   1500
aagttggccg cagtgttatc actcatggtt atggcagcac tgcataattc tcttactgtc   1560
atgccatccg taagatgctt ttctgtgact ggtgagtact caaccaagtc attctgagaa   1620
tagtgtatgc ggcgaccgag ttgctcttgc ccggcgtcaa tacgggataa taccgcgcca   1680
catagcagaa ctttaaaagt gctcatcatt ggaaaacgtt cttcggggcg aaaactctca   1740
aggatcttac cgctgttgag atccagttcg atgtaaccca ctcgtgcacc caactgatct   1800
tcagcatctt ttactttcac cagcgtttct gggtgagcaa aaacaggaag gcaaaatgcc   1860
gcaaaaaagg aataagggc gacacggaaa tgttgaatac tcatactctt ccttttcaa     1920 tcatgattga agcatttatc agggttattg tctcatgagc ggatacatat ttgaatgtat   1980
ttagaaaaat aaacaaatag gtcatgacca aaatccctta acgtgagttt tcgttccact   2040
gagcgtcaga ccccgtagaa aagatcaaag gatcttcttg agatcctttt tttctgcgcg   2100
taatctgctg cttgcaaaca aaaaaaccac cgctaccagc ggtggtttgt ttgccggatc   2160
aagagctacc aactcttttt ccgaaggtaa ctggcttcag cagagcgcag ataccaaata   2220
ctgtccttct agtgtagccg tagttaggcc accacttcaa gaactctgta gcaccgccta   2280
catacctcgc tctgctaatc ctgttaccag tggctgctgc cagtggcgat aagtcgtgtc   2340
ttaccgggtt ggactcaaga cgatagttac cggataaggc gcagcggtcg ggctgaacgg   2400
ggggttcgtg cacacagccc agcttggagc gaacgaccta caccgaactg agatacctac   2460
agcgtgagct atgagaaagc gccacgcttc ccgaagggag aaaggcggac aggtatccgg   2520
taagcggcag ggtcggaaca ggagagcgca cgagggagct tccaggggga aacgcctggt   2580
atctttatag tcctgtcggg tttcgccacc tctgacttga gcgtcgattt ttgtgatgct   2640
cgtcaggggg gcggagccta tggaaaaacg ccagcaacgc ggcctttta cggttcctgg    2700 ccttttgctg gccttttgct cacatgttct ttcctgcgtt atcccctgat tctgtggata   2760
```

```
accgtattac cgcctttgag tgagctgata ccgctcgccg cagccgaacg accgagcgca    2820
gcgagtcagt gagcgaggaa gcggaagagc gcctgatgcg gtattttctc cttacgcatc    2880
tgtgcggtat ttcacaccgc atatatggtg cactctcagt acaatctgct ctgatgccgc    2940
atagttaagc cagtatacac tccgctatcg ctacgtgact gggtcatggc tgcgccccga    3000
cacccgccaa cacccgctga cgcgccctga cgggcttgtc tgctcccggc atccgcttac    3060
agacaagctg tgaccgtctc cgggagctgc atgtgtcaga ggttttcacc gtcatcaccg    3120
aaacgcgcga ggcagctgcg gtaaagctca tcagcgtggt cgtgaagcga ttcacagatg    3180
tctgcctgtt catccgcgtc cagctcgttg agtttctcca gaagcgttaa tgtctggctt    3240
ctgataaagc gggccatgtt aagggcggtt ttttcctgtt tggtcactga tgcctccgtg    3300 taaggggat ttctgttcat gggggtaatg ataccgatga aacgagagag gatgctcacg    3360
atacgggtta ctgatgatga acatgcccgg ttactggaac gttgtgaggg taaacaactg    3420
gcggtatgga tgcggcggga ccagagaaaa atcactcagg gtcaatgcca gcgcttcgtt    3480
aatacagatg taggtgttcc acagggtagc cagcagcatc ctgcgatgca gatccggaac    3540
ataatggtgc agggcgctga cttccgcgtt tccagacttt acgaaacacg gaaaccgaag    3600
accattcatg ttgttgctca ggtcgcagac gttttgcagc agcagtcgct tcacgttcgc    3660
tcgcgtatcg gtgattcatt ctgctaacca gtaaggcaac cccgccagcc tagccgggtc    3720
ctcaacgaca ggagcacgat catgctagtc atgccccgcg cccaccggaa ggagctgact    3780
gggttgaagg ctctcaaggg catcggtcga gatcccggtg cctaatgagt gagctaactt    3840
acattaattg cgttgcgctc actgcccgct ttccagtcgg gaaacctgtc gtgccagctg    3900
cattaatgaa tcggccaacg cgcggggaga ggcggtttgc gtattgggcg ccagggtggt    3960
ttttcttttc accagtgaga cgggcaacag ctgattgccc ttcaccgcct ggccctgaga    4020
gagttgcagc aagcggtcca cgctggtttg ccccagcagg cgaaaatcct gtttgatggt    4080
ggttaacggc gggatataac atgagctgtc ttcggtatcg tcgtatccca ctaccgagat    4140
gtccgcacca acgcgcagcc cggactcggt aatggcgcgc attgcgccca gcgccatctg    4200
atcgttggca accagcatcg cagtgggaac gatgccctca ttcagcattt gcatggtttg    4260
ttgaaaaccg gacatggcac tccagtcgcc ttcccgttcc gctatcggct gaatttgatt    4320
gcgagtgaga tatttatgcc agccagccag acgcagacgc gccgagacag aacttaatgg    4380
gcccgctaac agcgcgattt gctggtgacc caatgcgacc agatgctcca cgcccagtcg    4440
cgtaccgtct tcatgggaga aaataatact gttgatgggt gtctggtcag agacatcaag    4500
aaataacgcc ggaacattag tgcaggcagc ttccacagca atggcatcct ggtcatccag    4560
cggatagtta atgatcagcc cactgacgcg ttgcgcgaga agattgtgca ccgccgcttt    4620
acaggcttcg acgccgcttc gttctaccat cgacaccacc acgctggcac ccagttgatc    4680
ggcgcgagat ttaatcgccg cgacaatttg cgacggcgcg tgcagggcca gactggaggt    4740
ggcaacgcca atcagcaacg actgtttgcc cgccagttgt tgtgccacgc ggttgggaat    4800
gtaattcagc tccgccatcg ccgcttccac ttttttcccgc gttttcgcag aaacgtggct    4860
ggcctggttc accacgcggg aaacggtctg ataagagaca ccggcatact ctgcgacatc    4920
gtataacgtt actggtttca cattcaccac cctgaattga ctctcttccg ggcgctatca    4980
tgccataccg cgaaaggttt tgcgccattc gatggtgtcc gggatctcga cgctctccct    5040
tatgcgactc ctgcattagg aagcagccca gtagtaggtt gaggccgttg agcaccgccg    5100
ccgcaaggaa tggtgcatgc aaggagatgg cgcccaacag tccccggcc acggggcctg    5160
```

-continued

```
ccaccatacc cacgccgaaa caagcgctca tgagcccgaa gtggcgagcc cgatcttccc    5220
catcggtgat gtcggcgata taggcgccag caaccgcacc tgtggcgccg gtgatgccgg    5280
ccacgatgcg tccggcgtag cctaggatcg agatcgatct cgatcccgcg aaattaatac    5340
gactcactat a                                                         5351
```

<210> SEQ ID NO 8
<211> LENGTH: 65
<212> TYPE: DNA
<213> ORGANISM: Artificial Sequence
<220> FEATURE:
<223> OTHER INFORMATION: Synthetic DNA

<400> SEQUENCE: 8

```
gctctagaaa gagggcgcgg cagagaagga ggaggtaaga aatgagtaat cgtaaatatt    60
tcggt                                                                65
```

<210> SEQ ID NO 9
<211> LENGTH: 50
<212> TYPE: DNA
<213> ORGANISM: Artificial Sequence
<220> FEATURE:
<223> OTHER INFORMATION: Synthetic DNA

<400> SEQUENCE: 9

```
cgccaacaat tccacacata gaaccaccac caacggcttt tactgcatcg                50
```

<210> SEQ ID NO 10
<211> LENGTH: 50
<212> TYPE: DNA
<213> ORGANISM: Artificial Sequence
<220> FEATURE:
<223> OTHER INFORMATION: Synthetic DNA

<400> SEQUENCE: 10

```
cgatgcagta aaagccgttg gtggtggttc tatgtgtgga attgttggcg                50
```

<210> SEQ ID NO 11
<211> LENGTH: 32
<212> TYPE: DNA
<213> ORGANISM: Artificial Sequence
<220> FEATURE:
<223> OTHER INFORMATION: Synthetic DNA

<400> SEQUENCE: 11

```
ccgctcgagt tactcaaccg taaccgattt tg                                   32
```

<210> SEQ ID NO 12
<211> LENGTH: 63
<212> TYPE: DNA
<213> ORGANISM: Artificial Sequence
<220> FEATURE:
<223> OTHER INFORMATION: Synthetic DNA

<400> SEQUENCE: 12

```
gctagatatt taaactatca cgacataagg aggtcaggga tgagtaatcg taaatatttc    60
ggt                                                                  63
```

<210> SEQ ID NO 13
<211> LENGTH: 65
<212> TYPE: DNA
<213> ORGANISM: Artificial Sequence
<220> FEATURE:

```
<223> OTHER INFORMATION: Synthetic DNA

<400> SEQUENCE: 13
gctctagacg acataacgtt agaaaagaat aaggtagttt catgagtaat cgtaaatatt    60
tcggt                                                                65

<210> SEQ ID NO 14
<211> LENGTH: 71
<212> TYPE: DNA
<213> ORGANISM: Artificial Sequence
<220> FEATURE:
<223> OTHER INFORMATION: Synthetic DNA

<400> SEQUENCE: 14
ccctaggatc gagatcgatc tcgatcccgc gaaattaata cgactcacta tattgacaat    60
taatcatccg g                                                         71

<210> SEQ ID NO 15
<211> LENGTH: 35
<212> TYPE: DNA
<213> ORGANISM: Artificial Sequence
<220> FEATURE:
<223> OTHER INFORMATION: Synthetic DNA

<400> SEQUENCE: 15
gctctagagg taatttttaa taataaagtt aatcg                               35
```